United States Patent [19]

Zasloff

[11] Patent Number: 5,567,681
[45] Date of Patent: Oct. 22, 1996

[54] PGLA AND XPF PEPTIDES AND USES THEREFOR

[75] Inventor: Michael A. Zasloff, Rockville, Md.

[73] Assignee: The United States of America as represented by the Department of Health and Human Services, Washington, D.C.

[21] Appl. No.: 834,992

[22] Filed: Feb. 14, 1992

Related U.S. Application Data

[63] Continuation of Ser. No. 731,304, Jul. 16, 1991, abandoned, which is a continuation of Ser. No. 81,793, Aug. 5, 1987, abandoned, which is a continuation-in-part of Ser. No. 76,734, Jul. 23, 1987, abandoned, which is a continuation-in-part of Ser. No. 21,493, Mar. 4, 1987, Pat. No. 4,810,777.

[51] Int. Cl.⁶ ............................................. A61K 38/17
[52] U.S. Cl. ........................ 514/13; 514/12; 514/2; 514/21; 514/934
[58] Field of Search ........................ 514/12, 13, 2, 514/21, 934; 530/324, 326

[56] References Cited

U.S. PATENT DOCUMENTS

| | | | |
|---|---|---|---|
| 3,883,499 | 5/1975 | Tachibana et al. | 530/328 |
| 3,928,306 | 12/1975 | Uchiyama et al. | 530/328 |

OTHER PUBLICATIONS

Giovannini e;t al, *Biochem. J.*, 243:113–120, 1987.
Csordas et al, *Toxicon* &;103–108, 1969.
Kaiser et al, *Proc. Natl. Acad. Sci. USA* 80:1137–1143, 1983.
Sures et al, Proc. Natl. Acad. Sco. USA 81:380–384, 1984.
CRC Handbook of Chemotherapeutic Agents vol. I pp. 178–185. "Peptide Antibiotics".
Kempf et al, *J. Biol. Chem.* 257:2469–2476, 1982.
Steiner et al, *Nature* 292:246–248, 1981.
Hoffmann et al, Embo, J. 2:711–714, 1983.
Richter et al, *Peptides* 6:17–21, 1985.
Andreu et al, *Biochem.* 149:531–535, 1985.
Merrifield et al, *Biochem.* 21:5020–5031, 1982.
Gibson et al, *J. Biol Chem.* 261:5341–5349, 1986.
The Merck Manual of Diagnosis and Therapy, 11th ed., pp. 761–778, (1966).

*Primary Examiner*—Christina Y. Chan
*Assistant Examiner*—T. Wessendorf
*Attorney, Agent, or Firm*—Elliot M. Olstein; Raymond J. Lillie

[57] ABSTRACT

The present invention relates to a method of producing antimicrobial effect by contacting a subject susceptible to microbial invasion or contamination, with antimicrobial amount of XPF and PGLa polypeptides.

10 Claims, No Drawings

PGLA AND XPF PEPTIDES AND USES THEREFOR

This application is a continuation of Ser. No. 07/731,304 filed Jul. 16, 1991 which is a continuation of Ser. No. 07/081,793 filed Aug. 5, 1987, now both abandoned which is a Continuation-In-Part of Ser. No. 07/076,734 filed Jul. 23, 1987, abandoned which in turn is a Continuation-In-Part of Ser. No. 07/021,493 filed Mar. 4, 1987, now U.S. Pat. No. 4,810,777.

BACKGROUND OF THE INVENTION

The present invention is related to a new method of producing bioactive effect. More particularly, the present invention is related to a method of producing anti-microbial effect by contacting a subject susceptible to microbial invasion or contamination, with antimicrobial amount of XPF and PGLa polypeptides.

Prior Art

XPF and PGLa polypeptides have been described in the literature and are characterized by the following amino acid sequence:

PGLa: GMASKAGAIAGKIAKVALKAL (NH$_2$)

XPF: GWASKIGQTLGKIAKVGLKELIQPK

A review of XPF and PGLa can be found in Hoffman et al, *EMBO J.* 2:711–714, 1983; Andreu et al, *J. Biochem.* 149:531–535, 1985; Gibson et al *J. Biol. Chem.* 261:5341–5349, 1986; and Giovannini et al, *Biochem. J.* 243:113–120, 1987. It should be noted that no function or useful property of these peptides has been identified in the literature.

SUMMARY OF THE INVENTION

It is, therefore, an object of the present invention to provide a new use of a known compound.

It is a further object of the present invention to provide a method of controlling, preventing or eradicating microbial growth or proliferation by contacting the microbes with antimicrobial amount of XPF and PGLa polypeptides.

It is yet another object of the present invention to provide a method of producing bioactive effect employing XPF and PGLa in bioactive amounts.

Other objects and advantages will become evident from the Detailed Description of the Invention.

DETAILED DESCRIPTION OF THE INVENTION

The above and various other objects and advantages of the present invention are achieved by a method of treating or controlling microbial growth, comprising administering to a host susceptible to microbial infection or contacting the microbes, directly or systemically, with antimicrobial amount of a polypeptide selected from the group consisting of XPF, PGLa and a combination thereof to prevent or eradicate microbial growth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

It is noted that various tests, methods, materials and the like to obtain the results described herein are the same as described in U.S. applications Ser. No. 07/021,493 filed Mar. 4, 1987 now U.S. Pat. No. 4,810,777 and Ser. No. 07/076,734 filed Jul. 23, 1987 which are incorporated herein by reference.

The term "bioactive" as used herein means having biological effect such as illustrated herein infra.

The term "antibiotic" as used herein means that the polypeptides employed in the present invention produce effects adverse to the normal biological functions of the cell, tissue or organism including death or destruction and prevention of the growth or proliferation of the biological system when contacted with said polypeptide.

The term "antimicrobial" as used herein means that the polypeptides employed in the present invention inhibit, prevent or destroy the growth or proliferation of microbes such as bacteria, fungi, virus and the like.

The term "substantially pure" as used herein means as pure as it is possible to obtain by using the methods known to one of ordinary skill in the art.

Of course, the amino acid sequence of the polypeptides being known, they can be routinely synthesized in substantially pure form by standard techniques well known in the art, such as by commercially available peptide synthesizers and the like. Such standard techniques of polypeptide synthesis can be found described in such publications as Merrifield, J. Chem. Soc. 85:2149–2154, 1963; Hunkapillar et al, Nature 310:105–111, 1984. XPF and PGLa were thus synthesized and obtained in substantially pure form as carboxyl-terminal amides.

Table 1 demonstrates the anti-bacterial activity of XPF and PGLa compared to Magainin. As can be seen, the three exhibit comparable activity against *E. coli*.

Table 2 shows the minimal inhibitory concentrations of XPF, PGLa and Magainin against different bacteria and fungi. As can be appreciated, the relative potencies of each of the peptides differs somewhat with respect to a particular organism, but the activity is quite similar.

Table 3 lists the minimal effective concentrations of XPF, PGLa and Magainin necessary to physically disrupt several different species of protozoa. In each case, the peptide induces osmotic swelling indicating a common mechanism.

TABLE 1

| Antimicrobial activity of peptides | |
|---|---|
| PEPTIDE | Zone of Inhibition on Lawn of *E. coli* Y1088 Generated by 50 µg of the peptide (mm) |
| MAGAININ II* | 10 |
| PGLa | 10 |
| XPF (NH$_2$) | 15 |

*Magainin II is a polypeptide characterized by the following amino acid sequence.
Magainin II: (NH$_2$)GIGKFLHSAKKFGKAFVGEIMNS(OH)

TABLE 2

SPECTRUM OF ANTI-MICROBIAL ACTIVITY OF SYNTHETIC PEPTIDES

| ORGANISM | MINIMAL INHIBITORY CONCENTRATION (μg/ml) | | |
|---|---|---|---|
| | Magainin II | PGLa | XPF |
| E. coli (25922) | 10–50 | 10–50 | 10–50 |
| P. aeruginosa (27883) | 50–100 | 200–500 | 50–100 |
| S. aureus (250230 | 500 | 50–100 | 100–200 |
| S. pyogenes (19615) | 10–50 | 10 | 10–50 |
| S. cerviscae (x2180) | 50–100 | 100–200 | 100–200 |
| C. albicans (14053) | 200–500 | 100–200 | 200–500 |

$10^5$ Organisms were inoculated from late-log phase cultures into 0.5 ml of TSB broth containing synthetic peptide at concentrations of 10, 50, 100, 200 and 500 μg/ml. Cultures were incubated at either 37° C. (bacteria) or 30° C. (fungi) for 24 hours. Concentrations of peptide at which no visible growth of innoculum occurred is listed.

TABLE 3

SENSITIVITY OF PROTOZOA TO SYNTHETIC PEPTIDES

| ORGANISM | MINIMAL DISRUPTIVE CONCENTRATION (μg/ml) | | |
|---|---|---|---|
| | Magainin II | PGLa | XPF |
| Paramecium caudatum | 10 | 5 | 10 |
| Tetrahymena pyriformis | 20 | 20 | 20 |
| Acanthameoba castellani | 2 | 2 | 2 |

Protozoa (about $10^2$) were suspended into 200 μl of 1% trypticase soy broth on a glass depression slide Actively growing cultures of *P. caudatum* and *T. pyrifomis* were obtained from Nasco (Wisc) and *A. castellani* from B Bowers (NHLBI). Peptides were added to various concentrations and the organism visually assessed by light microscopy within 15 minutes of exposure. The concentrations listed represent the minimal peptide concentration at which physical disruption of all protozoa occurred.

It is clear from the results presented herein that XPF and PGLa are potent antimicrobial agents.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A process for inhibiting, preventing, or destroying the growth of a bacterium or fungus in a host, comprising:

administering to a host at least one member selected from the group consisting of XPF peptide and PGLa peptide, said at least one member being administered in an amount effective to inhibit, prevent, or destroy the growth of a bacterium or fungus in a host.

2. The process of claim 1 wherein the said bacterium is inhibited, prevented or destroyed.

3. The process of claim 1 wherein the said fungus is inhibited, prevented or destroyed.

4. The process of claim 1 wherein said member is XPF peptide.

5. The process of claim 1 wherein said member is PGLa peptide.

6. A process for inhibiting, preventing, or destroying the growth of a bacterium or fungus, comprising:

contacting a bacterium or fungus with an effective antibacterial or antifungal amount of at least one member selected from the group consisting of XPF peptide and PGLa peptide.

7. The process of claim 6 wherein the said bacterium is inhibited, prevented or destroyed.

8. The process of claim 6 wherein the said fungus is inhibited, prevented or destroyed.

9. The process of claim 6 wherein said member is XPF peptide.

10. The process of claim 6 wherein said member is PGLa peptide.

* * * * *